United States Patent
Jensen et al.

(10) Patent No.: US 7,122,211 B2
(45) Date of Patent: Oct. 17, 2006

(54) METHODS FOR MANUFACTURING AN ENHANCED COSMETIC SKIN CARE TONER

(75) Inventors: Claude Jarkae Jensen, Cedar Hills, UT (US); Heidi Robinson, Orem, UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 09/836,870

(22) Filed: Apr. 17, 2001

(65) Prior Publication Data

US 2002/0187168 A1 Dec. 12, 2002

Related U.S. Application Data

(60) Provisional application No. 60/279,354, filed on Mar. 28, 2001.

(51) Int. Cl.
*A61K 6/00* (2006.01)
*A61K 36/00* (2006.01)

(52) U.S. Cl. ............ 424/725; 424/401; 424/776; 424/777; 514/848

(58) Field of Classification Search ............ 424/195.1, 424/401, 489, 404, 666, 725; 524/848, 844
See application file for complete search history.

(56) References Cited

U.S. PATENT DOCUMENTS 5,288,491 A * 2/1994 Moniz ............ 424/195.1
5,472,699 A * 12/1995 Duffy et al. ............ 424/401
6,436,449 B1 * 8/2002 Gidlund ............ 424/752
6,589,514 B1 * 7/2003 Jensen et al. ............ 424/59
2001/0033871 A1 * 10/2001 Gidlund ............ 424/725

FOREIGN PATENT DOCUMENTS

JP 2000-95663 A * 4/2000

OTHER PUBLICATIONS

Kodon et al., JP 2000-95663A, (2000), Translation. Paragraphs [0001-82, 0150-152].*
Dittmar, A., Morinda Citrifolia L. Use in Indigenous Samoan, (1993), J. Herbs Spices Medicianl Plants, 1(3) p. 77-91.*
Singh. Y. et al., Folk Medicine in Tonga, J. Ethnopharmacology, 12 (1984) 305-329.*
Nonidrink.com Advertisement, "Tahitian noni juice information about noni juice", www.nonidrink.com/skin_care.html, 1999.*
Lee, W., "MorindaNet plans for e-commerce", New Straights Times, Kuala LUmpur, (Jun. 1999).*
Nonidrink.com Advertisement, "Tahitian noni juice information about noni juice", www.nonidrink.com/skin_care.html, 1999.*
Talon et al., Derwent Acc. No. 2000-248448, (Mar. 17, 2000), abstract.*

* cited by examiner

*Primary Examiner*—Sreeni Padmanabhan
*Assistant Examiner*—Gina C. Yu
(74) *Attorney, Agent, or Firm*—Kirton & McConkie; Michael F. Krieger

(57) ABSTRACT

The present invention advances prior art toners by providing a toner formulated with *Morinda Citrifolia*, or Noni, from the Indian Mulberry plant. The addition of Noni to the toner of the present invention serves to provide significant skin care advantages not found in prior art toners.

40 Claims, No Drawings

METHODS FOR MANUFACTURING AN ENHANCED COSMETIC SKIN CARE TONER

RELATED APPLICATIONS

This application claims priority to U.S. Provisional Patent Ser. No. 60/279,354, filed on Mar. 28, 2001, and entitled "Tahitian Noni Enhanced Cosmetic Skin Care Toner."

BACKGROUND

1. Field of the Invention

The field of this invention relates to cosmetic products, and particularly to topical dermal toners. Specifically, the present invention relates to a topical dermal toner comprising a composition or formula containing *Morinda citrifolia* designed to contribute to the overall health of the skin and prepare the skin for further care.

2. Background

Cosmetic skin care products abound in the marketplace. These products, while differing in their ingredients or formulations, share a common goal in seeking to achieve and maintain healthy, youthful looking and feeling skin. Researchers and manufacturing companies have spent considerable time and expended significant resources in researching and advancing skin care products in order to provide the most complete and effective skin care possible. These advances have seen moderate to extensive success in terms of both their marketability as well as their actual ability to care for and improve the skin of their users. Despite these advances, several different types of ingredients can be found in the myriad of cosmetic skin care products currently available. This is largely attributable to the many different skin types or characteristics in existence from individual to individual. Indeed, several skin types exist requiring different ingredients for proper care. Common skin types include dry, oily, sensitive, or any combination of these commonly referred to as combination skin. As a result of these varying skin types, different and specific skin-type ingredients are needed to satisfy and care for the skin.

In addition to differing skin types contributing to the numerous ingredients found among skin care products, research is ongoing to find yet further improved ingredients or compositions of ingredients that improve overall skin care. This is especially true regarding facial skin care products as the face comprises a more sensitive area than other parts of the body and is more susceptible to damage due to, among other things, sunlight, makeup, and aging. As a result, many products claiming to perform separate and distinct functions for the overall care of the skin, and particularly for the face, have been introduced on the marketplace. Typically, a skin care regime for the face includes cleansing, toning, and moisturizing, in proper sequence. Other steps may be added, such as firming the skin with an intensive repair serum, and/or applying a nighttime face cream or moisturizer.

The skin is made up of several layers. The stratum corneum, the top layer, forms a protective covering for the skin and controls the flow of water and substances in and out of the skin. This is known as a barrier function. To stay healthy, the skin has to cope with changing environmental conditions and repair damages at the same time. The skin is in a constant state of repair as it sheds the dead cells on the surface and replenishes the lower layers.

The skin is often abused by soaps, emulsifier-based cosmetics, hot water, or organic solvents. These each contribute to rob the skin of essential moisture, and to create a stressed barrier that does not function properly. Moisture loss and irritation increases, leaving the skin sensitive, scaly, and dry. Free-radical activity multiplies, causing more wrinkles and premature aging.

Research shows that using a skin care product that includes the skin's natural building blocks speeds the skin's ability to repair itself and keeps the barrier function at optimal levels. This approach treats the problem, not the symptom. Irritation stops before it can start so recurring problems are avoided, thus bringing the skin back to ideal conditions.

The consumer demand for "natural" based products has been growing in recent years. Chemical synthesis is perceived as environmentally unsafe. A chemically synthesized ingredient may contain harsh chemicals. Natural products are perceived as pure and mild and superior to chemically synthesized products. Delivering a cosmetic benefit from plant sources, however, is not trivial. In order to derive a real benefit from a "natural" source, not only does a plant or a part of the plant containing a specific active have to be identified, but a minimum concentration and/or a specific extract of that plant has to be identified which truly delivers a cosmetic benefit.

The use of toners has been discovered to provide an indispensable part of proper and healthy skin care, especially facial care. Toners provide many advantages including removal of impure elements from the skin, such as sebum; that can clog pores, balance the pH levels of upset skin, refresh and rejuvenate the skin, smoothen and tighten pores, and prepare the skin for moisturizers. Toners typically comprise two types—balancing or hydrating toners.

Many prior art compositions of toners used for removing sebum from the skin of a user typically employ from 30 to 60 percent by weight of one or more of ethanol, acetone, and isopropanol. Ethanol, acetone and isopropanol, however, tend to defat the skin and remove the intercellular lipids critical for retaining moisture in the skin. Further, the sebum that is removed is replaced in as few as two to three hours on average. These compositions also frequently cause an unpleasant stinging sensation when applied.

Other prior art toners employ aqueous solutions of water-soluble glycol ethers for removing sebum from the skin of a user in the treatment of acne. The glycol ethers are present in the compositions in significant amounts, for example at 20–50 percent by weight. These glycol ether-based compositions are a vast improvement over the more typical alcohol- or acetone-based compositions, in that the glycol ethers dissolve sebum well and can provide for extended suppression of normal sebum levels, but do not dissolve the intercellular lipids in the skin or produce an unpleasant stinging sensation. One very significant drawback to the glycol ether-based toning compositions, however, is their disagreeable odor which is not easily masked by perfumes.

Moreover, in a large number of cases, toners may contain chemicals which may produce "irritation," including various inflammation symptoms or signs, when applied to the skin or mucosa. This may especially be true when applied to sensitive skin or certain other combination skin types.

In addition, many prior art toners contain compositions that do not provide sufficient barrier protection from harmful biological and environmental aging, while at the same time meeting the needs of the skin.

Therefore, what is needed is an alcohol-free toner that can help to protect the skins barrier repair and natural moisture, and that can help fight the harmful effects from daily agents tending to damage the skin.

SUMMARY AND OBJECTS OF THE INVENTION

The importance of using a toner in a daily skin care regime, as well as the advantages and benefits that stem from the introduction of *Morinda citrifolia* to the body, are recognized herein. As such, the present invention advances prior art toners by providing a toner formulated with *Morinda citrifolia*, or Tahitian Noni (Noni), produced by one or more parts of the Indian Mulberry plant. The addition of *Morinda citrifolia* to the toner of the present invention serves to provide significant skin care advantages not found in prior art toners.

Therefore, it is an object of the preferred embodiments of the present invention to provide a toner formulated with *Morinda citrifolia* as produced from one or more parts of the Indian Mulberry plant.

It is another object of the preferred embodiments of the present invention to provide a toner formulated with *Morinda citrifolia* that nourishes the health of the skin.

It is still another object of the preferred embodiments of the present invention to provide a toner formulated with *Morinda citrifolia* that helps to fight free radical damage.

It is a further object of the preferred embodiments of the present invention to provide a hydrating toner formulated with *Morinda citrifolia* that hydrates and restores moisture to the skin to maintain soft, supple, lustrous skin.

It is a further object of the preferred embodiments of the present invention to provide a toner formulated with *Morinda citrifolia* that refreshes and tones the skin without stripping essential elements from the skin.

It is a further object of the preferred embodiments of the present invention to provide a toner formulated with *Morinda citrifolia* that helps to normalize the hydration level of the skin.

It is a further object of the preferred embodiments of the present invention to provide a toner formulated with *Morinda citrifolia* that removes any last traces of surface impurities.

It is a further object of the preferred embodiments of the present invention to provide a toner formulated with *Morinda citrifolia* that promotes softness, comfort, radiance, and freshness in or to the skin.

It is a further object of the preferred embodiments of the present invention to provide a toner formulated with *Morinda citrifolia* that helps optimize application and absorption of subsequent skin care products.

It is yet another object of the preferred embodiments of the present invention to provide a toner formulated with *Morinda citrifolia* that restores normal pH levels and help to revitalize the skin.

It is yet another object of the preferred embodiments of the present invention to provide a toner formulated with *Morinda citrifolia* that refreshes and tones the skin.

It is yet another object of the preferred embodiments of the present invention to provide a toner formulated with *Morinda citrifolia* that purifies skin, tightens pores, and refines texture.

It is yet another object of the preferred embodiments of the present invention to provide a toner formulated with *Morinda citrifolia* that works with the skin's natural moisturizing factor to decrease oil production.

It is yet another object of the preferred embodiments of the present invention to provide a toner formulated with *Morinda citrifolia* that normalizes surface oils.

It is yet another object of the preferred embodiments of the present invention to provide a hydrating toner formulated with *Morinda citrifolia* to provide one or more of the above-mentioned objects.

It is finally an object of the preferred embodiments of the present invention to provide a balancing toner formulated with *Morinda citrifolia* to provide one or more of the above-mentioned objects.

The *Morinda citrifolia* enhanced toner of the present invention provides all of the beneficial functions of prior art toners such as, removal of surface impurities, revitalizing and smoothing the skin, restoring moisture to the skin, and preparing the skin for subsequent moisturizers or other cosmetics. In addition to these beneficial functions, the *Morinda citrifolia* enhanced toner of the present invention helps to minimize the visible signs of both biological and environmental aging, while at the same time, meeting the specific needs of the skin. *Morinda citrifolia* is high in antioxidants that help to fight free-radical damage caused by the sun and other elements. *Morinda citrifolia* is also rich in linoleic acid, which is an essential fatty acid with specific abilities for nourishing the health of the skin. Each of these, along with the other ingredients, aids in barrier repair and protection, or repair and protection of the stratum corneum.

To achieve the foregoing objects, and in accordance with the invention as embodied and broadly described herein, the present invention features a toner comprising several key ingredients. These ingredients comprise, among others, *Morinda citrifolia*, butylene glycol, zinc PCA, witch hazel, hydrolyzed algin and *chlorella vulgaris* extract (type 2-3), hypnea musciformis extract and mugwort (*artemisia vulgaris*). A portion of, or all of these ingredients may be combined with other ingredients commonly found in toners. In addition, a portion of, or all of these ingredients may be added to formulate a balancing or a hydrating toner.

DETAILED DESCRIPTION OF THE PREFERRED EMBODIMENTS

It will be readily understood that the components of the present invention, as generally described herein, could be arranged and designed in a wide variety of different formulations. Thus, the following more detailed description of the embodiments of the compositions or formulations of the present invention are not intended to limit the scope of the invention, as claimed, but are merely representative of the presently preferred embodiments of the invention.

I. General Discussion of Toners

On a daily basis, skin is exposed to damaging elements. These damaging elements include, among other things, makeup, sunlight, wind, and various particles existing in the air. Other elements, such as dead skin cells and sebum, are present on the surface of the skin as a result of the body's continuous replenishment of the skin at all levels. To maintain healthy skin, strict care and attention must be provided to ensure that these damaging elements are removed. Proper skin care helps to alleviate and reduce many of the damaging effects of these elements, such as aging, dryness, oiliness, blemishes, etc. To maintain healthy skin, a proper balance of both water and oil is essential.

A skin care regime usually entails a three-step process comprising cleansing, toning, and moisturizing: Each step requires a specific product and method of use. Cleansers are designed to remove dirt, cosmetics, and the normal skin byproducts, such as sebum, dead skin cells, and the like.

However, cleansers tend to leave residual elements on the skin, such as soap film and various oily components. In addition, many cleansers negatively affect the pH level of the skin. To remove these unwanted residual elements, toners have been developed, which are designed to remove the soap residue and other potential pore clogging elements, in addition to restoring proper pH levels and providing further skin care beyond mere cleansing. Thereafter, moisturizers serve to mimic the action of normal skin secretions in maintaining suppleness in the skin and provide a barrier to evaporation. The use of the moisturizer is necessitated by the removal of natural skin secretions by the cleanser and toner.

Toners typically exist as one of two types—balancing and hydrating.

Balancing Toners. Balancing toners seek to restore and maintain the normal pH levels found in the skin, while at the same time provide a refreshing look and feel to the skin. Balancing toners are also designed to control sebum and oil production, revitalize the skin, remove surface impurities without stripping moisture, help tighten pores thus smoothing and refining the skin's surface, restore lost minerals, prepare the skin for moisturizers or other cosmetics, and stimulate and refreshen the skin. In addition, depending upon the particular ingredient, balancing toners can oxygenate the skin's surface and help heal blemishes and broken capillaries.

As mentioned, cleansing can cause the pH levels of the skin to become upset, thus resulting in oily or overly dry skin. Therefore, as the skin possesses a natural pH level that is easily upset upon the introduction of moisturizers or other cosmetic skin care products, balancing toners have been developed to re-balance or restore the skin's acid mantle. However, because there are many substances that are stabilized with the skin's proper pH that can help restore the skin's acid mantle and refresh the skin, toner ingredients may vary. Moreover, due to the various skin types, it is important for users to make sure the balancing toner they are using is the right one for their skin type. It is easy to dehydrate the skin or cause oil glands to become overactive if the wrong toner is applied. For example, alcohol is the most drying ingredient found in many toners.

Some balancing toner formulations employ from 30 to 60 percent by weight of one or more of ethanol, acetone, isopropanol and denatured alcohol. Alcohols and acetone based compositions however, tend to defat the skin and remove the intercellular lipids critical for retaining moisture in the skin. In addition, these compositions tend to allow sebum and other pore clogging elements to return to the surface of the skin in just a short time.

To avoid this unnatural result, significant advances have been made where a number of balancing toner formulations have employed aqueous solutions of water-soluble glycol ethers. Glycol ethers may be present in the compositions in significant amounts, for example at 20–50 percent by weight. These glycol ether-based compositions are a vast improvement over the more typical alcohol or acetone-based compositions, in that the glycol ethers are more capable of dissolving the sebum and other surface elements that tend to clog the pores of the skin. In addition, glycol ether based compositions are capable of providing extended suppression of normal sebum levels without dissolving the intercellular lipids in the skin. Other non-alcohol toners have been formulated using deionized water, which acts as a solubilizer vehicle and provides a degree of moisturization.

Other balancing toner ingredients include glycerin, which acts as a moisturizer; alpha-hydroxy acids, which enhance the exfoliation of the skin's outer dead layer; panthenol; aloe vera; and coloring agents and/or fragrances. In addition, antioxidants have been added to some toners to help nourish the skin and protect it from premature aging caused by free radicals. It is known in the art that applying anti-oxidant vitamins to the skin helps to reduce the effects of aging. Adding vitamins, such as C, E and beta carotene, to the skin may significantly reduce the long-term damage caused by ultra-violet radiation. Balancing Toners can also include a number of various natural botanicals and extracts. One ordinarily skilled in the art will recognize that not all balancing toner ingredients are the same, and that various compositions and formulations may be obtained.

Hydrating Toners. The primary cause of skin damage and premature aging is the loss of moisture in the skin. The skin is continuously exposed to free radical damage from things such as the sun, pollutants and various chemicals. Exposure to these free radicals are damaging to the skin thus robbing the skin of its needed water content. This is known as dehydration. Dehydration constitutes a depletion of the moisture in the skin leaving it dull, splotchy, wrinkly, damaged, or practically speaking, "dry." Hydration or moisture is essential to soft, supple, lustrous, and generally healthy skin. As such, it is necessary to restore whatever moisture is lost in the skin and to maintain that moisture. This is the primary purpose of the third step in a typical skin care regime—use of a hydrating toner.

By employing a hydrating toner in a daily skin care regime, lost moisture is restored to the skin. Moreover, surface impurities are removed. Hydrating toners are also designed to control sebum and oil production, revitalize the skin, remove surface impurities without stripping moisture, help tighten pores thus smoothing and refining the skin's surface, restore lost minerals, and stimulate and refreshen the skin. In addition, depending upon the particular ingredient, hydrating toners can oxygenate the skin's surface and help heal blemishes and broken capillaries.

Moreover, due to the various skin types, it is important for users to make sure the hydrating toner they are using is the right one for their skin type. It is easy to dehydrate the skin or cause oil glands to become overactive if the wrong toner is applied. For example, alcohol is the most drying ingredient found in many toners.

Some hydrating toner formulations employ from 30 to 60 percent by weight of one or more of ethanol, acetone, isopropanol and denatured alcohol. As stated above, alcohols and acetone based compositions however, tend to defat the skin and remove the intercellular lipids critical for retaining moisture in the skin. In addition, these compositions tend to allow sebum and other pore clogging elements to return to the surface of the skin in just a short time.

To avoid this unnatural result, significant advances have been made where a number of hydrating toner formulations have employed aqueous solutions of water-soluble glycol ethers. Glycol ethers may be present in the compositions in significant amounts, for example at 20–50 percent by weight. These glycol ether-based compositions are a vast improvement over the more typical alcohol or acetone-based compositions, in that the glycol ethers are more capable of dissolving the sebum and other surface elements that tend to clog the pores of the skin. In addition, glycol ether based compositions are capable of providing extended suppression of normal sebum levels without dissolving the intercellular lipids in the skin. Non-alcohol toners have also been formulated using deionized or distilled water, which act as solubilizer vehicles and provide a degree of moisturization.

Other hydrating toner ingredients may include: glycerin, which acts as a moisturizer; alpha-hydroxy acids, which enhance the exfoliation of the skin's outer dead layer; panthenol; witch-hazel; aloe vera; various botanical extracts; various preservatives; and coloring agents and/or fragrances. In addition, antioxidants have been added to some toners to help nourish the skin and protect it from premature aging caused by free radicals. It is known in the art that applying anti-oxidant vitamins to the skin helps to reduce the effects of aging. Adding vitamins, such as C, E and beta carotene, to the skin may significantly reduce the long-term damage caused by ultra-violet radiation. Hydrating Toners can also include a number of various natural botanicals and extracts as well as antioxidants to calm irritated, dry skin.

A further primary function of hydrating toners, besides their moisture restoring and impurity removal functions, is to help prepare and normalize the skin for subsequent skin care treatments, such as additional moisturizers, etc.

Other ingredients. Toners may comprise several ingredients. One ordinarily skilled in the art will recognize that not all hydrating toner ingredients are the same, and that various compositions and formulations may be obtained.

Some of the various ingredients that may be used in the formulation of the present invention are discussed below.

A safe and effective amount of an anti-inflammatory agent may be added to the compositions of the subject invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone. The exact amount of anti-inflammatory agent to be used in the compositions will depend on the particular anti-inflammatory agent utilized since such agents vary widely in potency. Various steroidal anti-inflammatory agents, as well as non-steroidal anti-inflammatory agents may be used.

A safe and effective amount of a retinoid may be added to the compositions of the subject invention, preferably from about 0.001% to about 2.0%, more preferably from about 0.01% to about 0.1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid. The retinoid is preferably retinol, retinal, or retinoic acid, more preferably retinoic acid. The retinoids enhance the skin appearance benefits of the present invention. For example, the retinoids may diminish fine lines, wrinkles, or other textural discontinuities.

Antimicrobial agents, which is a compound capable of destroying microbes, may be used to prevent the development of microbes or prevent the pathogenic action of microbes. Antimicrobial agents are useful, for example, in controlling acne. A safe and effective amount of an antimicrobial agent may be added to compositions of the subject invention, preferably from about 0.001% to about 10%, more preferably from about 0.01% to about 5%, also from about 0.05% to about 2% or from about 0.05% to about 1% of the compositions. Preferred antimicrobial agents useful in the subject invention are benzoyl peroxide, erythromycin, tetracycline, clindamycin, azelaic acid, and sulfur resorcinol.

Some type of anti-oxidants or free-radical scavengers may be employed in the formulation. As mentioned, an anti-oxidant/radical scavenger provides protection against UV radiation which can cause increased scaling or texture changes in the stratum corneum and against other environmental agents which can cause skin damage. A safe and effective amount of an anti-oxidant/radical scavenger may be added to the compositions of the subject invention, preferably from about 0.1% to about 10%, more preferably from about 1% to about 5%, of the composition. Antioxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, amino-guanidine), sulfhydryl compounds (e.g., glutathione) and dihydroxy fumaric acid and its salts may be used.

Another ingredient is a sun screen agent. Specific suitable sunscreening agents include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxy-cimmamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4, 4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; 3-(4'-methylbenzylidene bornan-2-one) and 4-isopropyl-di-benzoylmethane. Of these, 2-ethylhexyl-p-methoxycinnamate, 4,4'-t-butyl methoxydibenzoylmethane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

A suitable amount of an organic hydroxy may be used. Organic hydroxy acids enhance the skin's appearance. For example, the organic hydroxy acids tend to improve the texture of the skin. Typical organic hydroxy acids include salicylic acid, glycolic acid, or lactic acid.

One ordinarily skilled in the art will recognize the many types of cosmetic agents and/or ingredients that may be used to compliment the toner compositions of the present invention formulated with *Morinda citrifolia*. Those mentioned herein are only examples, and are not meant to be limiting in any way.

II. General Discussion of Noni

The Indian Mulberry or Noni plant, known scientifically as *Morinda citrifolia* L., is a shrub or small tree up to 10 m in height. The leaves are oppositely arranged with an elliptic to ovate form. The small white flowers are contained in a fleshy, globose, head-like cluster. The fruits are large, fleshy, and ovoid. At maturity, they are creamy-white and edible, but have an unpleasant taste and odor. The plant is native to Southeast Asia and has spread in early times to a vast area from India to eastern Polynesia. It grows randomly in the wild, and it has been cultivated in plantations and small individual growing plots. The Noni flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds.

When fully ripe, the fruit has a pronounced odor like rancid cheese. Although the fruit has been eaten by several nationalities as food, the most common use of the Noni plant was as a red and yellow dye source. Recently, there has been an interest in the nutritional and health benefits of the Noni plant, further discussed below.

The present invention utilizes extracts and concentrated extracts from several various parts of the Indian Mulberry *Citrifolia* plant, including the leaves, bark, roots, fruit, seeds, and other parts of the plant. Preferably however, the present invention comprises processed *Morinda Citrifolia* in juice or oil form as it is obtained from the Indian Mulberry plant. In a currently preferred process of producing *Morinda Citrifolia* fruit juice, the fruit is either hand picked or picked by mechanical equipment. The fruit can be harvested when it is at least one inch (2–3 cm) and up to 12 inches (24–36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit can be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions. The *Morinda citrifolia* fruit juice and puree are preferably blended in a homogenous blend, after which they may be mixed with other ingredients, such as flavorings, sweeteners, nutritional ingredients, botanicals, and colorings. The finished fruit juice product is preferably heated and pasteurized at a minimum temperature of 181° F. (83° C.) or higher up to 212° F. (100° C.).

The product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp are further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, reverse osmosis filtration., and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp is preferably pasteurized at a temperature of 181° F. (83° C.) minimum and then packed in drums for further processing or made into a high fiber product.

The method for extracting and processing *Morinda citrifolia* seed oil is described in co-pending application Ser. No. 09/384,785, filed on Aug. 27, 1999, which is incorporated by reference herein. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

The Indian Mulberry, plant is rich in natural ingredients. Those ingredients that have been discovered include: from the leaves: alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; from the flowers:

acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta-rhamnosyl-glucopyranoside; from the fruit:

acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl) benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthio-propanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; from the roots: anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; from the root bark: alizarin, chlororubin, glycosides (pentose, hexose), morindadiol, morindanigrine, morindine, morindone, resinous matter, rubiadin monomethyl ether, and soranjidiol; from the wood: anthragallol-2,3-dimethylether; from the tissue culture: damnacanthal, lucidin, lucidin-3-primeveroside, and morindone-6beta-primeveroside; from the plant: alizarin, alizarin-alpha-methyl ether, anthraquinones, asperuloside, hexanoic acid, morindadiol, morindone, morindogenin, octanoic acid, and ursolic acid.

Recently, many health benefits have been discovered stemming from the use of products containing *Morinda citrifolia*. The benefit of *Morinda citrifolia* is found in its ability to isolate and produce Xeronine, which is a relatively small alkaloid physiologically active within the body. Xeronine occurs in practically all healthy cells of plants, animals and microorganisms. Even though *Morinda citrifolia* has a negligible amount of free xeronine, it contains appreciable amounts of the precursor of xeronine, called Proxeronine. Further, *Morinda citrifolia* contains the inactive form of the enzyme Proxeronase which releases Xeronine from proxeronine. A paper entitled, "The Pharmacologically Active Ingredient of Noni" by R. M. Heinicke of the University of Hawaii, indicates that *Morinda citrifolia* is "the best raw material to use for the isolation of xeronine," because of the building blocks of proxeronine and proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy.

Second, Xeronine protects and keeps the shape and suppleness of protein molecules so that they may be able to pass through the cell walls and be used to form healthy tissue. Without these nutrients going into the cell, the cell can not perform its job efficiently. Without pro-xeronine to produce xeronine our cells, and subsequently the body, suffer.

Third, Xeronine assists in enlarging the membrane pores of the cells. This enlargement allows for larger chains of peptides (amino acids or proteins) to be admitted into the cell. If these chains are not used they become waste.

Fourth, Xeronine, which is made from pro-xeronine, assists in enlarging the pores to allow better absorption of nutrients.

Each tissue has cells which contain proteins which have receptor sites for the absorption of xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifolia* in making a person feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifolia* has been known to provide a number of anecdotal effects in individuals having cancer, arthritis, headaches, indigestion, malignancies, broken bones, high blood pressure, diabetes, pain, infection, asthma, toothache, blemishes, immune system failure, and others.

In addition to the numerous health benefits, *Morinda citrifolia* also provides significant benefits to the skin. *Morinda citrifolia* is high in anti-oxidants that help to fight free-radical damage caused by the sun and other changing environmental conditions and elements. To stay healthy, the skin must cope with these elements and conditions and repair the damage caused at the same time. The skin is in a constant state of repair as it sheds the dead cells on the surface and replenishes the lower layers.

*Morinda citrifolia* is also especially rich in linoleic acid, which is an essential fatty acid having the specific ability to nourish the health of the skin. The skin is often abused by soaps, emulsifier-based cosmetics, hot water, organic solvents, etc., thus robbing essential moisture from the skin, and creating a stressed barrier that doesn't function properly. Moisture loss and irritation increases, leaving the skin sensitive, scaly, and dry. Free radical activity multiplies, causing more wrinkles and premature aging. *Morinda citrifolia* combats this problem by providing the essential fatty acids necessary to achieve and maintain healthy skin.

III. *Morinda Citrifolia* Enhanced Cosmetic Toner

The present invention advances prior art balancing toners by providing a toner formulated with *Morinda citrifolia*, or Tahitian Noni (Noni), from the Indian Mulberry plant. The recognized importance of using a toner in a daily skin care regime, as well as the recognized advantages and benefits that stem from the introduction of *Morinda citrifolia* to the body, combine to provide an advanced toner having significant skin care advantages.

The present invention features a *Morinda citrifolia* enhanced toner that provides all of the beneficial functions of prior art toners such as, removal of surface impurities, revitalizing and smoothing the skin, restoring and maintaining upset pH levels to the skin, and preparing the skin for subsequent moisturizers or other cosmetics. In addition to these beneficial functions, the *Morinda citrifolia* enhanced toner of the present invention helps to minimize the visible signs of both biological and environmental aging, while at the same time, meeting the specific needs of the skin. *Morinda citrifolia* is high in antioxidants that help to fight free-radical damage caused by the sun and other elements. *Morinda citrifolia* is also rich in linoleic acid, which is an essential fatty acid with specific abilities for nourishing the health of the skin. Each of these, along with the other ingredients, aids in barrier repair and protection, or repair and protection of the stratum corneum.

The present invention features a toner comprising several key ingredients to compliment the presence of *Morinda citrifolia*, an active ingredient. These other ingredients include, but are not limited to, Zinc PCA, witch hazel, hydrolyzed algin and *chlorella vulgaris* extract (type 2-3), hypnea musciformis extract and mugwort (*artemisia vulgaris*). Each is discussed below in greater detail.

The first key ingredient in the enhanced toner of the present invention, and the unique ingredient, is *Morinda citrifolia*. As discussed, *Morinda citrifolia* provides many benefits to the body, including the skin. *Morinda cirtifolia* fruit juice is present in an amount from about 0.1–80 percent by weight. *Morinda citrifolia* oil extract may also be present in an amount from about 0.1–10 percent by weight of the total composition or formulation. A suitable carrier, such as water, is also present in an amount from about 20–80 percent by weight.

Another key ingredient is Zinc PCA. This ingredient is typically employed in a toner for normal to combination skin, but may also be used in various other quantities in other types of toners. Zinc PCA works naturally with the skin to inhibit sebum or oil production.

Another key ingredient is witch hazel. Witch hazel acts as an astringent to purify and refresh the skin. Witch hazel is also a UVB absorber as well as serving to destroy free-radicals present within and on the skin's surface.

Another key ingredient to the present invention is hydrolyzed algin and *chlorella vulgaris* extract (type 2-3). These ingredients neutralize the effects of many environmental pollutants known to cause significant damage to the skin and to contribute to premature aging. Algin and *chlorella* also exhibit excellent short and long term moisturizing properties which further guards against free-radical activity to help preserve the health of the skin.

Another key ingredient is hypnea musciformis extract and mugwort (*artemisia vulgaris*). These ingredients serve to calm irritations caused by exposure of the skin to chemicals and UV rays.

A portion of, or all of these ingredients may be combined with other ingredients commonly found in toners. The natural ingredient blend of antioxidants serve to help stop and repair free radical damage. The *Morinda citrifolia* extract, along with other ingredients such as Gingko biloba extract, grape seep extract, mushroom extract (rich in ergothioneine, which aids in skin repair from UV damage), and vitamins E, C, and A all contribute to the prevention of free-radical activity and help to repair the damage caused by free-radical activity.

As there exists two types of toners, balancing and hydrating, the ingredients of the present invention are designed to be incorporated into formulations for each. Each of these key ingredients can be added to those specific for formulating either a balancing or a hydrating toner as discussed above.

In addition to the key ingredient outlined above, and to the specific ingredients that make up either a balancing or a hydrating toner, one skilled in the art will appreciate that various preservatives can be added to the formulation in sufficient quantities. These preservatives can include the esters of p-hydroxybenzoic acid, such as methyl p-hydroxybenzoate, and propyl p-hydroxybenzoate; cis-1-(3-chloroally)-3,5,7-triaza-1-azoniaadamantane chloride; ethylenediaminetetraacetic acid (EDTA) and salts of EDTA; imidazolidinyl urea; and the like or any combination thereof. The total amount of preservative used can vary, but usually it is from about 0.3 to about 1.0 percent.

Color and essence can also be included in the formulation as desired. Color additives may include both natural and artificial dyes, such as carotenoid derivatives, D+C or F, D+C colors, and the like, while essences can include any non-irritating natural and artificial oils, perfumes, and the like.

The following are examples of toner formulations comprising *Morinda citrifolia* therein to create an improved toner formulation for various skin types. These examples are merely illustrative and are not meant to be limiting in any way.

EXAMPLE ONE

| Ingredients | Percent by Weight |
| --- | --- |
| Noni (*Morinda citrifolia*) Fruit Juice | 30–40% |
| Water | 30–40% |
| Glycerin | 0–1% |
| Alcohol Denatured | 0–1% |
| Butylene Glycol | 0–1% |
| Sodium Chloride | 0–1% |
| Dipotassium Phosphate | 0–1% |
| Sodium Citrate | 0–1% |
| Panthenol (pro-vitamin B5) | 0–1% |
| Diazolidinyl urea | 0–1% |
| PPG-26-Buteth-26 | 0–1% |
| Benzophenone-4 | 0–1% |
| Citric Acid | 0–1% |
| Disodium EDTA | 0–1% |
| Potassium Phosphate | 0–1% |
| PEG-40 Hydrogenated Castor Extract | 0–1% |
| Caprylolyl Salicylic Acid (beta-hydroxy acid) | 0–1% |
| Fragrance | 0–1% |
| PEG-115M | 0–1% |
| Cabbage Rose Water | 0–1% |
| FD & C Red No. 4 | 0–1% |
| D & C Red No. 33 | 0–1% |

EXAMPLE TWO

| Ingredients | Percent by Weight |
| --- | --- |
| Noni (*Morinda citrifolia*) Fruit Juice | 30–40% |
| Water | 30–40% |
| Alcohol Denat | 0–1% |
| Butylene Glycol | 0–1% |
| Glycerin | 0–1% |
| Silica Dimethyl Silylate | 0–1% |
| Zinc Oxide | 0–1% |
| Propylene Glycol | 0–1% |
| PEG-60 Hydrogenated Castor Extract | 0–1% |
| methylparaben | 0–1% |
| Lactic Acid | 0–1% |
| Grapefruit Extract | 0–1% |
| Fragrance | 0–1% |
| Menthoxypropanediol | 0–1% |
| Hexylene Glycol | 0–1% |
| Witch Hazel | 0–1% |

EXAMPLE THREE

| Ingredients | Percent by Weight |
| --- | --- |
| Noni (*Morinda citrifolia*) Fruit Juice | 30–40% |
| Water | 30–40% |
| SD Alcohol 40 | 0–1% |
| Witch Hazel Distillate | 0–1% |
| PEG-40 Hydrogenated Castor Oil | 0–1% |
| Fragrance | 0–1% |
| Aloe Vera Gel | 0–1% |
| Allantoin | 0–1% |
| Menthyl lactate | 0–1% |
| Sorbitol | 0–1% |
| Sodium Lactate | 0–1% |
| Proline | 0–1% |
| Sodium PCA | 0–1% |
| Hydrolyzed Collagen | 0–1% |
| FD & C Blue No. 1 | 0–1% |
| FD & C Yellow No. 5 | 0–1% |

EXAMPLE FOUR

| Ingredients | Percent by Weight |
| --- | --- |
| Noni (*Morinda citrifolia*) Fruit Juice | 30–40% |
| Water | 30–40% |
| Glycerin | 0–1% |
| PEG-8 | 0–1% |
| PEG-40 | 0–1% |
| Hydrogenated Castor Oil | 0–1% |
| Polyaminopropyl Biquanide | 0–1% |
| Panthenol | 0–1% |
| Niacinamide | 0–1% |
| Aloe Barbadensis Gel | 0–1% |
| *Matricaria* (*Chamoilla Recutita*) Extract | 0–1% |
| Propylene Glycol | 0–1% |
| Polyquaternium-10 | 0–1% |
| Ethoxydiglycol | 0–1% |
| Fragrance | 0–1% |
| EDTA | 0–1% |
| Sodium Hydroxide | 0–1% |
| Methylparaben | 0–1% |

EXAMPLE FIVE

| Ingredients | Percent by Weight |
| --- | --- |
| Noni (*Morinda citrifolia*) Fruit Juice | 30–40% |
| Water | 30–40% |
| SD Alcohol 40-B | 0–1% |
| Dipropylene Glycol | 0–1% |
| Witch Hazel (*Hamamelis Virfiniana*) Distillate | 0–1% |
| Hops (*Humulus Lupulus*) Extract | 0–1% |
| Rosemary (*Rosmarinus Officinalis*) Extract | 0–1% |
| *Swertia Japonica* Extract | 0–1% |
| Tocopheryl Acetate (vitamin E Acetate) | 0–1% |
| Panthenol | 0–1% |
| Aloe Barbadensis Extract | 0–1% |
| Pyridoxine HCL | 0–1% |
| Farnesol | 0–1% |
| Salicylic Acid | 0–1% |
| Menthol | 0–1% |
| Glycerin | 0–1% |
| Fragrance | 0–1% |
| Butylene Glycol | 0–1% |
| Sodium Hydroxide | 0–1% |

EXAMPLE SIX

| Ingredients | Percent by Weight |
| --- | --- |
| Noni (*Morinda citrifolia*) Fruit Juice | 30–40% |
| Water | 30–40% |
| SD Alcohol 40-B | 0–1% |
| Witch Hazel Distillate | 0–1% |
| Menthol | 0–1% |
| Aloe Barbadensis Extract | 0–1% |
| Glycerin | 0–1% |
| Diglycerin | 0–1% |
| *Eucalyptus Globulus* Oil | 0–1% |
| Fragrance | 0–1% |
| Butylene Glycol | 0–1% |
| PG | 0–1% |
| Ext. Violet 2 | 0–1% |
| Green 5 | 0–1% |

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed is:

1. A method for making a topical cosmetic skin toner composition, said method comprising the steps of:
   obtaining processed *Morinda citrifolia* fruit juice, wherein said fruit juice includes Proxeronine;
   obtaining processed *Morinda citrifolia* seed oil extract;
   combining said processed *Morinda citrifolia* fruit juice, and *Morinda citrifolia* oil seed extract with a at least one ingredient selected from a balancing toner ingredient and a hydrating toner ingredient to create said topical cosmetic skin toner composition, wherein said juice is present between about 0.1 and 80 percent by weight and said seed oil extract is present between about 0.1 and 10 percent by weight.

2. The method of claim 1, wherein said release of Xeronine occurs from the interaction of said Proxeronine and at least one of:
   (i) Proxeronase present in said fruit juice; and
   (ii) Proxeronase present in said skin.

3. The method of claim 1, wherein said *Morinda citrifolia* fruit juice is present in said topical cosmetic skin toner composition in an amount between 10–15 percent by weight.

4. The method of claim 1, wherein said *Morinda citrifolia* fruit juice is present in said topical cosmetic skin toner composition in an amount between 15–20 percent by weight.

5. The method of claim 1, wherein said *Morinda citrifolia* fruit juice is present in said topical cosmetic skin toner composition in an amount between 20–25 percent by weight.

6. The method of claim 1, wherein said *Morinda citrifolia* fruit juice is present in said topical cosmetic skin toner composition in an amount between 25–30 percent by weight.

7. The method of claim 1, wherein said *Morinda citrifolia* fruit juice is present in said topical cosmetic skin toner composition in an amount between 30–35 percent by weight.

8. The method of claim 1, wherein said *Morinda citrifolia* fruit juice is present in said topical cosmetic skin toner composition in an amount between 35–40 percent by weight.

9. The method of claim 1, wherein said *Morinda citrifolia* fruit juice is present in said topical cosmetic skin toner composition in an amount between 40–45 percent by weight.

10. The method of claim 1, wherein said *Morinda citrifolia* fruit juice is present in said topical cosmetic skin toner composition in an amount between 45–50 percent by weight.

11. The method of claim 1, wherein said *Morinda citrifolia* fruit juice is present in said topical cosmetic skin toner composition in an amount between 50–55 percent by weight.

12. The method of claim 1, wherein said *Morinda citrifolia* fruit juice is present in said topical cosmetic skin toner composition in an amount between 55–60 percent by weight.

13. The method of claim 1, wherein said *Morinda citrifolia* fruit juice is present in said topical cosmetic skin toner composition in an amount between 60–65 percent by weight.

14. The method of claim 1, wherein said *Morinda citrifolia* fruit juice is present in said topical cosmetic skin toner composition in an amount between 65–70 percent by weight.

15. The method of claim 1, wherein said *Morinda citrifolia* fruit juice is present in said topical cosmetic skin toner composition in an amount between 70–75 percent by weight.

16. The method of claim 1, wherein said *Morinda citrifolia* fruit juice is present in said topical cosmetic skin toner composition in an amount between 75–80 percent by weight.

17. The method of claim 1, further comprising the step for combining water in said topical cosmetic skin toner composition, wherein said water is present in an amount between about 20–80 percent by weight.

18. The method of claim 1, further comprising the step for combining one or more additional ingredients into said topical cosmetic skin toner composition, wherein said one or more additional ingredients are selected from the group consisting of glycerin, alcohol denatured, butylene glycol, sodium chloride, dipotassium phosphate, sodium citrate, panthenol (pro-vitamin B5), diazolidinyl urea, PPG-26-Buteth-26, benzophenone-4, citric acid, disodium EDTA, potassium phosphate, PEG-40 hydrogenated castor extract, capryloyl salicylic acid (beta-hydroxy acid), fragrance, PEG-115M, cabbage rose water, FD & C Red No. 4, and D&C Red No. 33.

19. The method of claim 1, further comprising the step for combining one or more additional ingredients into said topical cosmetic skin toner composition, wherein said one or more additional ingredients are selected from the group consisting of alcohol denatured, butylene glycol, glycerin, silica dimethyl silylate, zinc oxide, propylene glycol, PEG-60 hydrogenated castor extract, methylparaben, lactic acid, grapefruit extract, fragrance, menthoxypropanediol, hexylene glycol, and witch hazel.

20. The method of claim 1, further comprising the step for combining one or more additional ingredients into said topical cosmetic skin toner composition, wherein said one or more additional ingredients are selected from the group consisting of SD alcohol 40, witch hazel distillate, PEG-40, hydrogenated castor oil, fragrance, aloe vera gel, allantoin, menthyl lactate, sorbitol, sodium lactate, proline, sodium PCA, hydrolyzed collagen, FD&C Blue No. 1, and FD&C Yellow No. 5.

21. The method of claim 1, further comprising the step for combining one or more additional ingredients into said topical cosmetic skin toner composition, wherein said one or more additional ingredients are selected from the group consisting of glycerin, PEG-8, PEG-40, hydrogenated castor oil, polyaminopropyl biguanide, panthenol, niacinamide, aloe barbadensis gel, matricaria (Chamomilla Recutita) extract, propylene glycol, polyquaternium-10, ethoxydiglycol, fragrance, EDTA, sodium hydroxide, and methylparaben.

22. The method of claim 1, further comprising the step for combining one or more additional ingredients into said topical cosmetic skin toner composition, wherein said one or more additional ingredients are selected from the group consisting of SD alcohol 40-B, dipropylene glycol, witch hazel (Hamamelis Virfiniana) distillate, hops (*Humulus lupulus*) extract, rosemary (*Rosmarinus Officinalis*) extract, swertiajaponica extract, tocopheryl acetate (vitamin E Acetate), panthenol, aloe barbadensis extract, pyridoxine HCL, farnesol, salicylic acid, menthol, glycerin, fragrance, butylene glycol, and sodium hydroxide.

23. The method of claim 1, further comprising the step for combining one or more additional ingredients into said topical cosmetic skin toner composition, wherein said one or more additional ingredients are selected from the group consisting of SD alcohol 40-B, witch hazel distillate, menthol, aloe barbadensis extract, glycerin, diglycerin, eucalyptus globulus oil, fragrance, butylene glycol, PG, Ext. D&C Violet 2, and D&C Green 5.

24. A method for hydrating skin, said method comprising
applying said cosmetic skin toner composition made according to claim 1 to said skin to.

25. A method for hydrating and treating skin, the method comprising
applying said composition made according to claim 1 to said skin.

26. The method of claim 24, wherein said release of Xeronine occurs from the interaction of said Proxeronine and at least one of:
(i) Proxeronase present in said fruit juice; and
(ii) Proxeronase present in said skin.

27. The method of claim 24, wherein said *Morinda citrifolia* fruit juice is present in said topical cosmetic skin toner composition in an amount between 10–15 percent by weight.

28. The method of claim 24, wherein said *Morinda citrifolia* fruit juice is present in said topical cosmetic skin toner composition in an amount between 15–20 percent by weight.

29. The method of claim 24, wherein said *Morinda citrifolia* fruit juice is present in said topical cosmetic skin toner composition in an amount between 20–25 percent by weight.

30. The method of claim 24, wherein said *Morinda citrifolia* fruit juice is present in said topical cosmetic skin toner composition in an amount between 25–30 percent by weight.

31. The method of claim 24, wherein said *Morinda citrifolia* fruit juice is present in said topical cosmetic skin toner composition in an amount between 30–35 percent by weight.

32. The method of claim 24, wherein said *Morinda citrifolia* fruit juice is present in said topical cosmetic skin toner composition in an amount between 35–40 percent by weight.

33. The method of claim 24, wherein said *Morinda citrifolia* fruit juice is present in said topical cosmetic skin toner composition in an amount between 40–45 percent by weight.

34. The method of claim 24, wherein said *Morinda citrifolia* fruit juice is present in said topical cosmetic skin toner composition in an amount between 45–50 percent by weight.

35. The method of claim 24, wherein said *Morinda citrifolia* fruit juice is present in said topical cosmetic skin toner composition in an amount between 50–55 percent by weight.

36. The method of claim 24, wherein said *Morinda citrifolia* fruit juice is present in said topical cosmetic skin toner composition in an amount between 55–60 percent by weight.

37. The method of claim 24, wherein said *Morinda citrifolia* fruit juice is present in said topical cosmetic skin toner composition in an amount between 60–65 percent by weight.

38. The method of claim 24, wherein said *Morinda citrifolia* fruit juice is present in said topical cosmetic skin toner composition in an amount between 65–70 percent by weight.

39. The method of claim 24, wherein said *Morinda citrifolia* fruit juice is present in said topical cosmetic skin toner composition in an amount between 70–75 percent by weight.

40. The method of claim 24, wherein said *Morinda citrifolia* fruit juice is present in said topical cosmetic skin toner composition in an amount between 75–80 percent by weight.

* * * * *